United States Patent
Liu et al.

(10) Patent No.: US 9,635,458 B2
(45) Date of Patent: Apr. 25, 2017

(54) HEART RATE DETECTION METHOD USED IN EARPHONE AND EARPHONE CAPABLE OF DETECTING HEART RATE

(71) Applicant: Goertek, Inc., Weifang, ShanDong Province (CN)

(72) Inventors: Song Liu, Weifang (CN); Bo Li, Weifang (CN); Na Li, Weifang (CN); Shasha Lou, Weifang (CN)

(73) Assignee: Goertek, Inc., Weifang, Shandong Province (CN)

( * ) Notice: Subject to any disclaimer, the term of this patent is extended or adjusted under 35 U.S.C. 154(b) by 0 days.

(21) Appl. No.: 14/901,564

(22) PCT Filed: May 29, 2015

(86) PCT No.: PCT/CN2015/080201
§ 371 (c)(1),
(2) Date: Dec. 28, 2015

(87) PCT Pub. No.: WO2016/011848
PCT Pub. Date: Jan. 28, 2016

(65) Prior Publication Data
US 2016/0212530 A1    Jul. 21, 2016

(30) Foreign Application Priority Data

Jul. 24, 2014 (CN) .......................... 2014 1 0354577
Aug. 25, 2014 (CN) .......................... 2014 1 0422000
Aug. 25, 2014 (CN) .......................... 2014 1 0422876

(51) Int. Cl.
*H04R 1/10* (2006.01)
*H04R 3/00* (2006.01)
(Continued)

(52) U.S. Cl.
CPC ......... *H04R 3/005* (2013.01); *A61B 5/02438* (2013.01); *A61B 5/02444* (2013.01);
(Continued)

(58) Field of Classification Search
CPC ............ H04R 2420/00; H04R 2460/00; H04R 2201/00; H04S 2420/00; A61B 5/024;
(Continued)

(56) References Cited

U.S. PATENT DOCUMENTS

2010/0125218 A1* 5/2010 Haartsen ............ A61B 5/02438
600/528
2014/0114201 A1* 4/2014 Watanabe ............ A61B 5/6898
600/485

FOREIGN PATENT DOCUMENTS

CN     102215740        7/2014
JP     2009153822 A  *  7/2009   .......... A61B 5/0245

OTHER PUBLICATIONS

PCT/CN2015/080201,Written Opinion of the International Searching Authority dated Sep. 9, 2015, 4 pages and English Translation, 3 pages.

* cited by examiner

*Primary Examiner* — Leshui Zhang
(74) *Attorney, Agent, or Firm* — Boyle Fredrickson, S.C.

(57) ABSTRACT

The present invention discloses a heart rate detection method used in an earphone and an earphone capable of detecting heart rate. The method comprises: providing a cavity inside the earphone and installing a microphone in the cavity; a shell of the earphone is provided with a hole at a position where an opening of the cavity clings to, and when the earphone is worn, the cavity and the auricle which the hole clings to form an enclosed space; collecting signals generated by pressure change in the cavity by the microphone when the earphone is worn; and detecting heart rate
(Continued)

according to the signals collected by the microphone. According to the technical scheme of the invention, the microphone is placed in the enclosed cavity formed by the cavity in the earphone and the shell of the earphone, which reduces interference of external noises, and reinforces signal information collected by the microphone.

15 Claims, 8 Drawing Sheets

(51) Int. Cl.
    *A61B 5/024*     (2006.01)
    *A61B 5/00*     (2006.01)
    *H04R 29/00*     (2006.01)

(52) U.S. Cl.
    CPC .......... *A61B 5/6803* (2013.01); *A61B 5/6817* (2013.01); *H04R 1/1016* (2013.01); *H04R 1/1091* (2013.01); *H04R 29/00* (2013.01); *A61B 2562/0204* (2013.01)

(58) Field of Classification Search
    CPC ..... A61B 5/08; A61B 5/02438; A61B 5/6816; A63B 24/00
    USPC ... 381/74, 26, 309, 311, 72, 122, 91, 56, 57, 381/58; 600/528, 529, 512, 513, 514, 28; 700/94
    See application file for complete search history.

HEART RATE DETECTION METHOD USED IN EARPHONE AND EARPHONE CAPABLE OF DETECTING HEART RATE

TECHNICAL FIELD

The invention relates to the field of earphone and heart rate detection technology, particularly to a heart rate detection method used in an earphone and an earphone capable of detecting heart rate.

DESCRIPTION OF RELATED ART

With the continuous development of social economy, people's material standard of living improves with each passing day, and people are paying more attention to their health. Heart rate detection will provide very important information on health for people. Any display of abnormal heart rate will indicate a problem of health, thus heart rate detection can find out whether or not our body has a problem without delay. Heart rate detection can also reflect to some extent whether or not human's motion intensity is appropriate. In order to achieve the optimum effect of exercise, people should keep their heart rate within a certain scope in the course of exercise, and the heart rate detection can provide an index for a reasonable amount of exercise.

In addition, lots of people like wearing an earphone to listen to music during exercise. In order to detect the heart rate during exercise without the need to carry around other devices, people start to study relevant technology of how to detect heart rate by using an earphone. For heart rate detection technology, in addition to heart rate belt, a technology of detecting heart rate by using an earphone emerges at present to achieve the purpose of convenience and accuracy.

The technology of detecting heart rate by using an earphone just emerged in recent years. On Oct. 23 to 25, 2013, Kaiteki Corporation and Bifrostec Corporation exhibited a technology of detecting pulse fluctuation by using an earphone at a health-equipment exhibition in Yokohama, Japan. The technology uses the earphone closely clinging to the auditory meatus to form an enclosed space, and a certain pressure will be generated in the auditory meatus because of vibration of the eardrum, and the pressure will change with the change of vibration. Information of the pressure change in the auditory meatus will be collected by a microphone, thus the purpose of detecting heart rate can be achieved. However, the earphone cannot occupy the entire auditory meatus, which will cause a leak of the air in the auditory meatus, and, as a result, the microphone cannot detect the change of the pressure and the heart rate detection will be interfered by external noises.

BRIEF SUMMARY OF TUE INVENTION

In view of aforesaid problem, the present invention provides a heart rate detection method used in an earphone and an earphone capable of detecting heart rate to overcome aforesaid problem or at least partly solve aforesaid problem.

The present invention provides a heart rate detection method used in an earphone. The method comprises: providing a cavity inside the earphone, and installing a first microphone in the cavity; the position where an opening of the cavity clings to a shell of the earphone is the position where the shell of the earphone clings to an auricle of a wearer when the earphone is worn; the earphone shell is provided with a hole at a position where the opening of the cavity clings to, and when the earphone is worn, the cavity and the auricle which the hole clings to form an enclosed space; collecting signals generated by pressure change in the cavity by the first microphone when the earphone is worn; taking the signals collected by the first microphone as signals related to heart rate; and detecting heart rate according to the signals related to heart rate.

Optionally, the method further comprises: installing a second microphone in the earphone head of the earphone; when the earphone is worn, collecting signals generated by an earphone loudspeaker in the earphone head by the second microphone; performing self-adaptive filtering process on the signals collected by the second microphone to obtain first estimated signals of the signals generated by the earphone loudspeaker in the signals collected by the first microphone; and subtracting the first estimated signals from the signals collected by the first microphone to obtain the signals related to heart rate.

Optionally, the method further comprises: installing a third microphone in the earphone at a position where the earphone does not contact the skin of the wearer; when the earphone is worn, collecting the external interference signals by the third microphone; performing self-adaptive filtering process on the signals collected by the third microphone to obtain second estimated signals of external interference signals in the signals collected by the first microphone; then taking the signals collected by the first microphone as signals related to heart rate comprising: subtracting the second estimated signals from the signals collected by the first microphone to obtain the signals related to heart rate; and subtracting the first estimated signals from the signals collected by the first microphone to obtain the signals related to heart rate comprising: subtracting the first estimated signals and the second estimated signals from the signals collected by the first microphone to obtain the signals related to heart rate.

The present invention also provides an earphone capable of detecting heart rate, wherein the earphone comprises: a heart rate detection unit, a cavity provided in the earphone, and a first microphone installed in the cavity;

wherein the position where an opening of the cavity clings to a shell of the earphone is the position where the shell of earphone clings to an auricle of a wearer when the earphone is worn; the earphone shell is provided with a hole at a position where the opening of the cavity clings to, and when the earphone is worn, the cavity and the auricle which the hole clings to form an enclosed space; the first microphone is used for collecting signals generated by pressure change in the cavity when the earphone is worn; the signals collected by the first microphone are taken as signals related to heart rate; and the heart rate detection unit is used for detecting heart rate according to the signals related to heart rate.

Optionally, the earphone also comprises: a first subtractor, a first self-adaptive filtering unit, and a second microphone installed in the earphone head of the earphone; the second microphone, for collecting signals generated by the earphone loudspeaker and outputting the signals to the first self-adaptive filtering unit; the first self-adaptive filtering unit, for performing self-adaptive filtering process on the signals collected by the second microphone according to the signals related to heart rate, and after obtaining first estimated signals of the signals generated by the earphone loudspeaker in the signals collected by the first microphone, outputting the first estimated signals to the first subtractor; the first subtractor, for subtracting the first estimated signals from the signals collected by the first microphone, obtaining the signals related to heart rate and outputting the signals to the heart rate detection unit and the first self-adaptive filtering unit.

Optionally, the earphone also comprises: a second subtractor, a second self-adaptive filtering unit, and a third microphone installed in the earphone at a position where the earphone does not contact the skin of the wearer; the third microphone, for collecting the external interference signals and outputting the signals to the second self-adaptive filtering unit when the earphone is worn; the second self-adaptive filtering unit, for performing self-adaptive filtering process on the signals collected by the third microphone according to the signals related to heart rate, after obtaining second estimated signals of external interference signals in the signals collected by the first microphone, outputting the second estimated signals to the second subtractor; the second subtractor, for subtracting the second estimated signals from the signals collected by the first microphone, obtaining the signals related to heart rate and outputting the signals to the heart rate detection unit and the second self-adaptive filtering unit; or for subtracting the second estimated signals from the signals collected by the first microphone that have subtracted the first estimated signals, obtaining the signals related to heart rate and outputting the signals related to heart rate to the heart rate detection unit, the second self-adaptive filtering unit and the first self-adaptive filtering unit.

As can be seen from the foregoing, the technical scheme in the embodiment of the invention uses the enclosed cavity formed by the cavity in the earphone and the earphone shell to place the microphone, which reduces interference of external noises, and reinforces signal information collected by the microphone. The second microphone is added to the earphone for collecting signals generated by the earphone loudspeaker, and the self-adaptive filter is designed to further eliminate the influence of the signals generated by the earphone loudspeaker on heart rate detection. And the third microphone is added to the earphone for collecting the external interference signals, and the self-adaptive filter is designed to further eliminate the influence of the external interference signals on heart rate detection.

Above description is only a summary of the technical scheme of the present invention. In order to know the technical means of the present invention more clearly so that it can be put into effect according to the content of the description, and to make the aforesaid and other purpose, features and advantages of the invention clearer, the embodiments of the invention will be described in further detail with reference to the drawings.

DETAILED DESCRIPTION OF THE INVENTION

The exemplary embodiments of the present disclosure are described in further detail with reference to the drawings below. Although the drawings show the embodiments of the present disclosure, it should be understood that the disclosure can be implemented in various forms and is not intended to be limited by the embodiments described here. On the contrary, the embodiments are provided to make the invention understood more thoroughly and completely convey the scope of the disclosure to a person skilled in the art.

Figure 1:
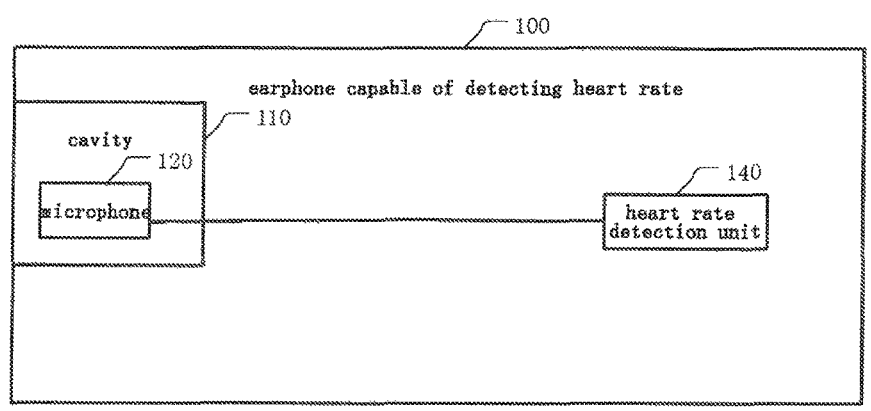
FIG. 1 is a structural diagram of an earphone capable of detecting heart rate in the embodiment of the present invention.

FIG. 1 is a structural diagram of an earphone capable of detecting heart rate in the embodiment of the present invention. As is shown in FIG. 1, the earphone 100 capable of detecting heart rate comprises: a heart rate detection unit 140, a cavity 110 provided in the earphone, and a microphone 120 installed in the cavity 110;

Wherein the position where an opening of the cavity 110 clings to a shell of the earphone is the position where the shell of the earphone clings to an auricle of a wearer when the earphone is worn; the shell of the earphone is provided with a hole at a position where the opening of the cavity 110 clings to, and when the earphone is worn, the cavity and the auricle which the hole clings to form an enclosed space;

the microphone 120, for collecting signals generated by pressure change in the cavity 110 when the earphone is worn;

the heart rate detection unit 140, for detecting heart rate according to the signals collected by the microphone 120.

In the earphone 100 capable of detecting heart rate shown in FIG. 1, the small cavity 110 is provided in the earphone 100 to place the microphone 120 and forms an enclosed space with the auricle, which reduces interference of external noises, and reinforces signal information collected by the microphone 120.

In an embodiment of the invention, the heart rate detection unit 140, for detecting the cycle of the signals which are collected by the microphone and have been filtered, and obtaining heart rate from the reciprocal of the detected cycle of the signals.

In prior arts of earphone detecting heart rate, the microphone is generally directly placed in the earphone at a position just directed at the auditory meatus, for collecting pressure change information in the ear cavity generated by vibration of the eardrum. But on the one hand, since the space formed by the earphone and auditory meatus is large, a leak of the air in the auditory meatus will be caused, thus the pressure change information collected by the microphone is very weak; on the other hand, generally the earphone cannot occupy the entire auditory meatus, thus there will be interference from external noises if the microphone is directly placed in the earphone. Therefore, for the earphone shown in FIG. 1 of the invention, another way to install the microphone is designed; see FIG. 2A-2C for specifics.

Figure 2A:
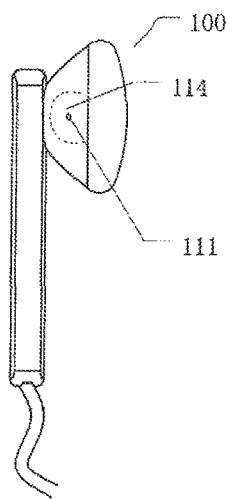
FIG. 2A is a lateral schematic diagram of an earphone 100 provided with a cavity 110 in an embodiment of the present invention.
Figure 2B:
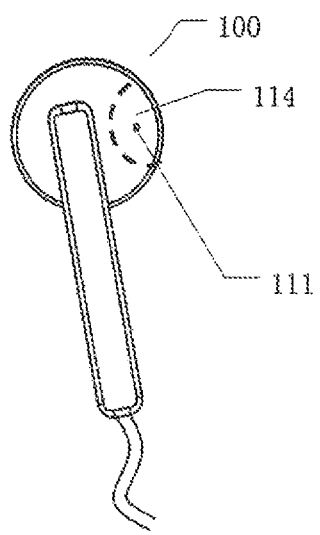
FIG. 2B is a back schematic diagram of an earphone 100 provided with a cavity 110 in an embodiment of the present invention.
Figure 2C:
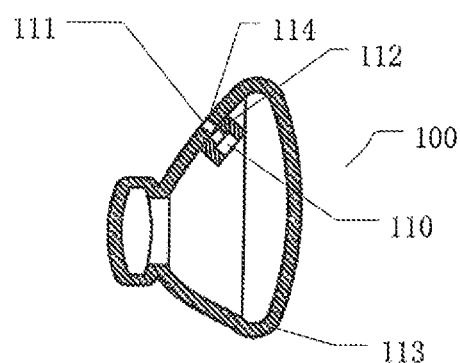
FIG. 2C is a lateral section view of an earphone 100 provided with a cavity 110 in an embodiment of the present invention.

FIG. 2A is a lateral schematic diagram of an earphone 100 provided with a cavity 110 in an embodiment of the present invention. FIG. 2B is a back schematic diagram of an earphone 100 provided with a cavity 110 in an embodiment of the present invention. FIG. 2C is a lateral section view of an earphone 100 provided with a cavity 110 in an embodiment of the present invention. In order to better collect useful signals related to heartbeat, the present invention designs a small cavity for placing the microphone. See FIG. 2A and FIG. 2B, the scope in the dashed line shown in the figure shows the position 112 of the cavity 110 formed inside the earphone. See FIG. 2C, an opening of the cavity 110 clings to the earphone shell 113. As can be seen, in the embodiment, the cavity 110 is at the edge of the earphone at a position 114 close to the auricle, and the earphone is provided with a hole 111 at the position where the earphone clings to the cavity. When the earphone is worn, the hole 111 tightly clings to the auricle, thus the cavity 110 and the part of the auricle that presses close to the cavity form an enclosed space. The microphone is installed in the cavity 110, and shrink and vibration of the auricle wall will cause change of the pressure in the cavity 110, thus the microphone will collect the pressure change information in the cavity 110. The information reflects the frequency of heartbeats to some extent, thus heart rate can be detected hereby.

In physics, for an enclosed space (without regard to temperature), intensity of pressure is inversely proportional to volume. That is to say, the smaller the volume, the larger the intensity of pressure, and the larger the pressure acting on a certain area. When a user wears the earphone, an enclosed space is formed in the auditory meatus, and the fluctuation of pulse pressure of the vessel will cause shrink of the ear wall, thus certain pressure change will be generated in the cavity. The pressure change signal will be detected by the microphone. Generally speaking, the fluctuation of pulse pressure of the vessel is very weak. The larger the enclosed space, the smaller the pressure change that can be detected by the microphone. In order to enhance the intensity of the pressure change detected by the microphone, the embodiment installs the microphone in an enclosed small cavity and the small cavity clings closely to the auditory meatus. Since the fluctuation of pulse pressure of the vessel causes shrink and vibration of the ear wall, the vibration makes the microphone in the small cavity detect change of the pressure. And the design of the small cavity will reduce the influence of external interference signals.

Figure 3:
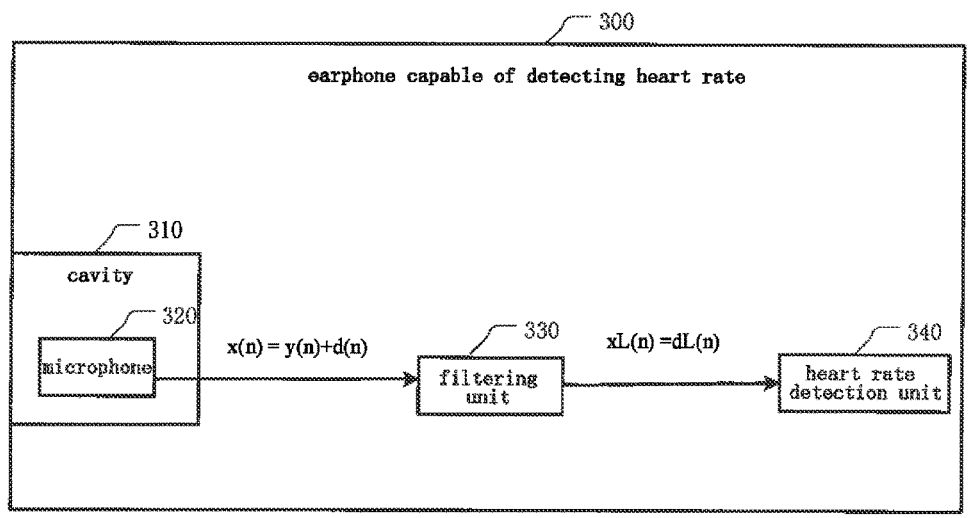
FIG. 3 is a structural diagram of an earphone capable of detecting heart rate in another embodiment of the present invention.

FIG. 3 is a structural diagram of an earphone capable of detecting heart rate in another embodiment of the present invention. As is shown in FIG. 3, the earphone 300 capable of detecting heart rate comprises: a filtering unit 330, a heart rate detection unit 340, a cavity 310 provided in the earphone, and a microphone 320 installed in the cavity 310;

Wherein the position where an opening of the cavity 310 clings to a shell of the earphone is the position where the shell of the earphone clings to the auricle of a wearer when the earphone is worn; the shell of the earphone is provided with a hole at a position where the opening of the cavity 310 clings to, and when the earphone is worn, the cavity and auricle which the hole clings to form an enclosed space;

the microphone 320, for collecting signals generated by pressure change in the cavity 310 when the earphone is worn, and outputting the corresponding signals to the filtering unit 330. The filtering unit 330, for performing filtering process on the signals collected by the microphone 320, obtaining the filtered signals and outputting the signals to the heart rate detection unit 340. Here the filtering unit filters the signals collected by the microphone 320 to eliminate the influence of the interfering noise on heart rate detection. The heart rate detection unit 340 is for detecting heart rate according to the filtered signals.

In an embodiment of the invention, the heart rate detection unit 340, for detecting the cycle of the signals related to heart rate, and obtaining heart rate from the reciprocal of the detected cycle of the signals. For example, the heart rate detection unit 340 can detect the cycle of the signals related to heart rate by using autocorrelation method and threshold value method, etc.

In an embodiment of the invention, the filtering unit 330 shown in FIG. 3 comprises: a low pass filter, for performing low pass filtering process on signals collected by the microphone 320 to filter out high-frequency interference signal. This is because that the frequency of pulse vibration is relatively low (0.3 Hz-3 Hz or so) while the frequency of external noise is higher.

According to this feature, the influence of external high-frequency noise can be eliminated via the low pass filter. For example, the low pass filter can be an FIR filter of which the cut-off frequency is 5 Hz.

In the earphone shown in FIG. 3, the low pass filter is adopted to perform low pass filtering process on signals collected by the microphone. As is shown in FIG. 3, first the microphone in the small cavity is used for collecting the pressure signals in the cavity; then the low pass filter is used for performing low pass filtering on the signals collected by the microphone; at last, after the heart rate signal is obtained, heart rate can be detected. The beat of heart has certain periodicity, thus heart rate signal is a signal with certain periodicity. The cycle corresponding to the signal can be obtained according to autocorrelation method, and the reciprocal of the cycle is heart rate.

The specific process is as follows:

Suppose the signal detected by the microphone is: $x(n)=y(n)+d(n)$; wherein $y(n)$ represents interference signal; $d(n)$ represents the pressure change signal generated by the flow of blood; and n represents sampling time point;

After low pass filtering, the signal of $x(n)$ becomes: $xL(n)=dL(n)$. The external noise signal collected by the microphone will be filtered out after low pass filtering. After $dL(n)$ is obtained, according to the periodicity characteristic of the signal, the cycle can be detected by using autocorrelation method, threshold value method, etc, and the reciprocal of the cycle is heart rate.

Via the earphone in the embodiment shown in FIG. 1 or FIG. 3, heart rate of human under various conditions (still, moving, etc) can be obtained, so that the information of physical condition of human body can be obtained, or on this basis human can control their amount of exercise within an appropriate scope in accordance with specific conditions.

On the basis of aforesaid embodiment, the heart rate detection method used in an earphone of the present invention is provided.

Figure 4:
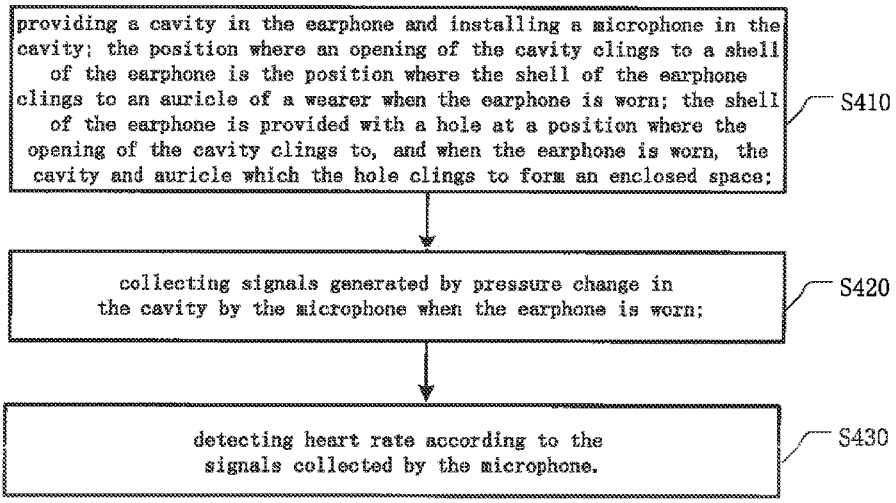
FIG. 4 is a flowchart showing a heart rate detection method used in an earphone in the embodiment of the present invention.

FIG. 4 is a flowchart showing a heart rate detection method used in an earphone in the embodiment of the present invention. As is shown in FIG. 4, the method comprises:

Step S410, providing a cavity in the earphone and installing a microphone in the cavity; the position where an opening of the cavity clings to a shell of the earphone is the position where the shell of the earphone clings to an auricle of a wearer when the earphone is worn; the shell of the earphone is provided with a hole at a position where the opening of the cavity clings to, and when the earphone is worn, the cavity and auricle which the hole clings to form an enclosed space.

Step S420, when the earphone is worn, collecting signals generated by pressure change in the cavity by the microphone.

Step S430, detecting heart rate according to the signals collected by the microphone, that is, taking the signals collected by the microphone as signals related to heart rate; and detecting the heart rate according to the signals related to heart rate.

In an embodiment of the invention, before Step S430, the method shown in FIG. 4 further comprises: performing filtering process on the signals collected by the microphone and obtaining the filtered signals. Then detecting heart rate according to the signals collected by the microphone in Step S430 comprises: detecting heart rate according to the filtered signals.

In an embodiment of the invention, performing filtering process on the signals collected by the microphone of the method shown in FIG. 4 comprises: performing low pass filtering process on the signals collected by the microphone to filter out the high-frequency interference signal.

In an embodiment of the invention, detecting heart rate according to the filtered signals comprises: detecting the cycle of the filtered signals, and obtaining the heart rate from the reciprocal of the detected cycle of the signals.

In summary, the beneficial effect of the technical scheme of aforesaid embodiment of the present invention comprises that: (1) The enclosed cavity of a relatively small volume is used for placing the microphone, which reduces interference of external noises, and reinforces signal information detected by the microphone. (2) According to the feature of the frequency of pulse vibration, a low pass filter is designed to further reduce the influence of external high-frequency noise.

In addition, using earphone to detect heart rate has another critical problem, that is, it is inevitable to be influenced by the signals (for example, music or voice, etc) generated by the earphone loudspeaker, which will greatly influence the detection of heart rate. Thus, the following solution is provided.

Figure 5:
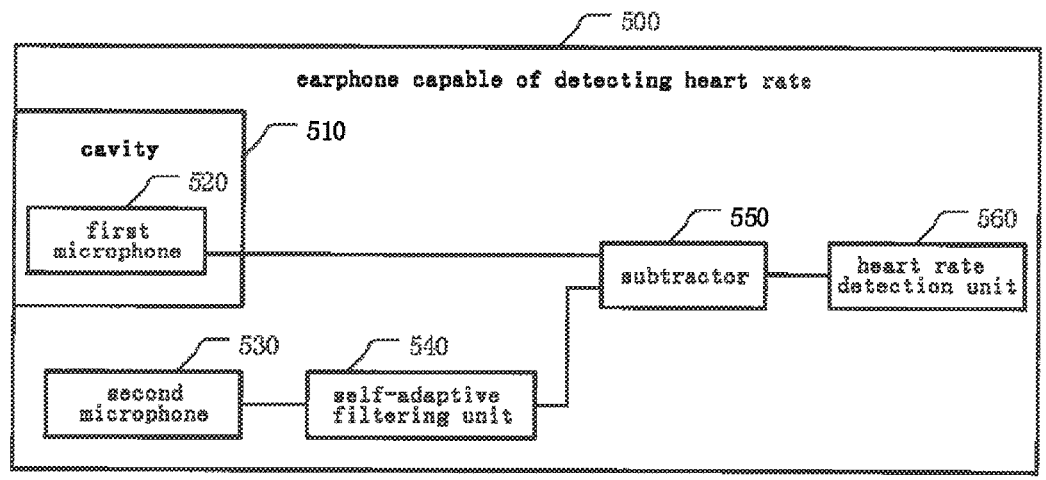
FIG. 5 is a structural diagram of an earphone capable of detecting heart rate in the embodiment of the present invention.

FIG. 5 is a structural diagram of an earphone capable of detecting heart rate in the embodiment of the present invention. As is shown in FIG. 5, the earphone 500 capable of detecting heart rate comprises: a subtractor 550, a heart rate detection unit 560, a self-adaptive filtering unit 540, a cavity 510 provided in the earphone, a first microphone 520 installed in the cavity 510, and a second microphone 530 installed in the earphone head of the earphone;

wherein the position where an opening of the cavity 510 clings to a shell of the earphone is the position where the earphone shell clings to an auricle of a wearer when the earphone is worn; the shell of the earphone is provided with a hole at a position where the opening of the cavity 510 clings to, and when the earphone is worn, the cavity and the auricle which the hole clings to form an enclosed space.

The first microphone 520 is for collecting signals generated by pressure change in the cavity 510 and outputting the signals to the subtractor 550 when the earphone 500 is worn. The second microphone 530 is for collecting signals generated by the earphone loudspeaker and outputting the signals to the self-adaptive filtering unit 540 when the earphone is worn. The self-adaptive filtering unit 540 is for performing self-adaptive filtering process on the signals collected by the second microphone 530 according to the signals related to heart rate, and after obtaining first estimated signals of e signals generated by the earphone loudspeaker in the signals collected by the first microphone 520, outputting the first estimated signals to the subtractor 550. The subtractor 550 is for subtracting the first estimated signals outputted by the self-adaptive filtering unit 540 from the signals collected by the first microphone 520, obtaining the signals related to heart rate and outputting the signals to the heart rate detection unit 560 and the self-adaptive filtering unit 540. The heart rate detection unit 560 is for detecting heart rate according to the signals related to heart rate.

The first microphone 520 will collect the signals generated by the earphone loudspeaker while collecting signals generated by pressure change in the cavity 510. Thus self-adaptive filtering process is performed on the signals detected by the second microphone 530 in FIG. 5, so that the signals generated by the earphone loudspeaker in the signals collected by the first microphone 520 can be accurately estimated according to the signals generated by the earphone loudspeaker collected by the second microphone 530, and the purpose is to eliminate the influence of the signals generated by the earphone loudspeaker on the heart rate detection. The first microphone 520 and the second microphone 530 both will detect the signals generated by the earphone loudspeaker. The cycles of the two kinds of signals are the same, but amplitudes are different, thus a self-adaptive filter is needed to be used for eliminating this difference, so that the signals generated by the earphone loudspeaker can be eliminated from the signals collected by the first microphone 520 to obtain effective heart rate information.

In the earphone 500 capable of detecting heart rate shown in FIG. 5, the cavity 510 is arranged in the earphone 500 for placing the first microphone 520, which reduces interference of external noises, and reinforces signal information collected by the first microphone 520. But the first microphone 520 will inevitably collect the signals generated by the earphone loudspeaker. Thus, the earphone 500 capable of detecting heart rate adds the second microphone 530 to collect the signals generated by the earphone loudspeaker, and performs self-adaptive filtering on the signals collected by the second microphone 530, and subtracts the second microphone signals after self-adaptive filtering from the signals collected by the first microphone 520, and then detects heart rate. Thereby the influence of the signals generated by the earphone loudspeaker on the heart rate detection is further eliminated.

In an embodiment of the invention, the earphone shown in FIG. 5 further comprises a low pass filter, for performing low pass filtering process on the signals collected by the first microphone 520, obtaining the low pass filtered signals and outputting the signals to the subtractor 550. That is, the subtractor 550 is for subtracting the first estimated signals outputted by the self-adaptive filtering unit 540 from the low pass filtered signals, obtaining signals related to heart rate and outputting the signals to the heart rate detection unit 560. This is because that the frequency of pulse vibration is relatively low (0.3 Hz-3 Hz or so) while the frequency of external noise is higher. According to this feature, the influence of external high-frequency noise can be eliminated via the low pass filter. For example, the low pass filter can be an FIR filter of which the cut-off frequency is 5 Hz. The specific structures of the cavity 510 arranged in the earphone and the first microphone 520 installed in the cavity 510 are similar to the structures shown in FIG. 2A-2C, thus it will not be repeated here.

Figure 6:
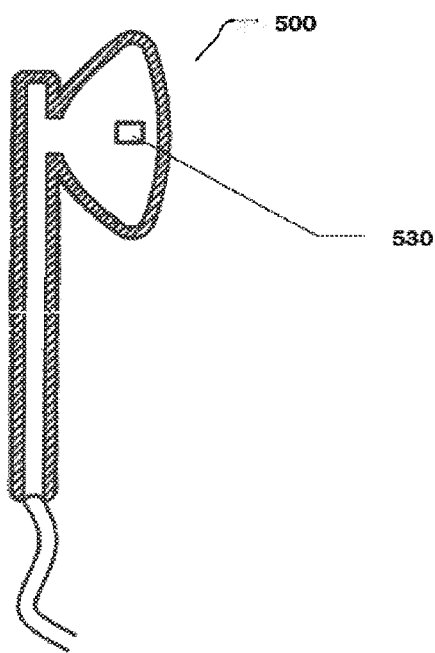
FIG. 6 is a diagram showing the installing position of a second microphone in an embodiment of the present invention.

FIG. 6 is a diagram showing the installing position of a second microphone in an embodiment of the present invention. In the embodiment the second microphone 530 is installed in the earphone head of the earphone. See FIG. 6, the second microphone 530 can be arranged at the position of the earphone 500 shown in FIG. 6, and then the earphone loudspeaker coordinates with the earphone shell, forming a cavity in front of the earphone loudspeaker, and the second microphone 530 can be arranged in the cavity. Preferably, the second microphone 530 is arranged in front of the vibrating diaphragm of the earphone loudspeaker and there is an interval between the second microphone 530 and the vibrating diaphragm, so that the second microphone is situated on the transmission path of the sound wave when the earphone loudspeaker produces sound, and the second microphone and the earphone loudspeaker will not affect each other.

In practice, even if the earphone can occupy the entire auditory meatus to form a completely enclosed cavity, the influence of the signals generated by the earphone loudspeaker on heart rate detection is inevitable, because the earphone loudspeaker is contained in the earphone head. Thus the signals generated by the earphone loudspeaker will inevitably be detected by the first microphone. Then the data collected by the first microphone comprises not only the pressure change information generated by the fluctuation of pulse pressure of the vessel, but also the signals generated by the earphone loudspeaker. In order to eliminate the influence of the signals generated by the earphone loudspeaker collected by the first microphone on heart rate detection, the present invention adds a second microphone in the earphone, and the second microphone is installed in the earphone head, for example, the position of the earphone shown in FIG. 6. The second microphone is used for collecting the signals generated by the earphone loudspeaker. There is a strong correlation between the signals generated by the earphone loudspeaker collected by the first microphone and the signals generated by the earphone loudspeaker collected by the second microphone, and on this basis a certain filter can be adopted to eliminate the influence of the signals generated by the earphone loudspeaker.

According to the foregoing analysis, if the signals generated by the earphone loudspeaker can be eliminated from the signals detected by the first microphone, then the signals generated by the shrink of the auditory meatus caused by flow of blood can be obtained. The signals are relevant to the frequency of heartbeat, and heart rate information can be obtained based on the signals. There is a strong correlation between the signals generated by the earphone loudspeaker collected by the first microphone and the signals generated by the earphone loudspeaker collected by the second microphone, but the two are not entirely equal. The signals collected by the second microphone cannot be directly taken out from the signals collected by the first microphone, thus the embodiment filters out the interference generated by external noises in the method of self-adaptive filtering.

In summary, in the embodiment of the invention: first, the enclosed cavity of a relatively small volume is used for placing the microphone, which reduces interference of external noises, and reinforces signal information detected by the first microphone. Second, the second microphone is added to the earphone for collecting signals generated by the earphone loudspeaker, and the self-adaptive filter is designed to further eliminate the influence of the signals generated by the earphone loudspeaker on heart rate detection. Furthermore, according to the feature of the frequency of pulse vibration, a low pass filter is designed to further reduce the influence of external high-frequency noise. It will be further described below with FIG. 7 as an example.

Figure 7:
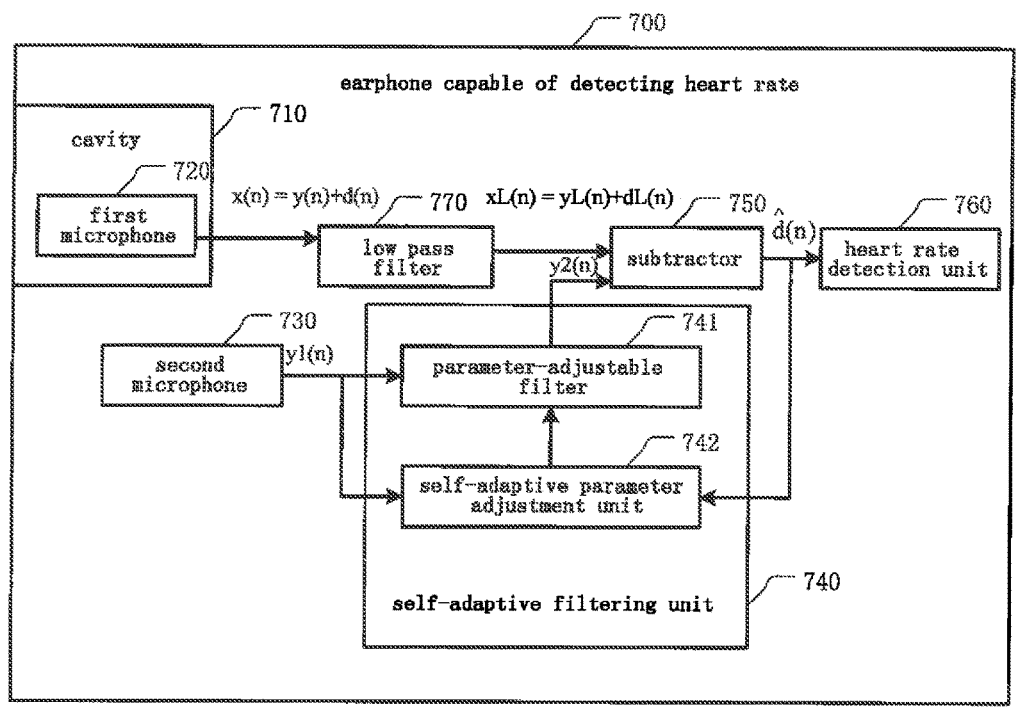
FIG. 7 is a structural diagram of an earphone capable of detecting heart rate in another embodiment of the present invention.

FIG. 7 is a structural diagram of an earphone capable of detecting heart rate in another embodiment of the present invention. As is shown in FIG. 7, the earphone 700 capable of detecting heart rate comprises: a subtractor 750, a heart rate detection unit 760, a low pass filter 770, a second microphone 730 installed in the earphone head of the earphone, a self-adaptive filtering unit 740, a cavity 710 provided in the earphone and a first microphone 720 installed in the cavity 710. Wherein the self-adaptive filtering unit 740 comprises: a parameter-adjustable filter 741 and a self-adaptive parameter adjustment unit 742.

Wherein the position where an opening of the cavity 710 clings to a shell of the earphone is the position where the shell of the earphone clings to an auricle of a wearer when the earphone is worn; the earphone shell is provided with a hole at a position where the opening of the cavity 710 clings to, and when the earphone is worn, the cavity and the auricle which the hole clings to form an enclosed space.

The first microphone 720 is used for collecting signals generated by pressure change in the cavity 710 and outputting the signals to the low pass filter 770 when the earphone 700 is worn. The first microphone 720 will collect the signals generated by the earphone loudspeaker while collecting signals generated by pressure change in the cavity 710. The low pass filter 770 is for performing low pass filtering process on signals collected by the first microphone 720 and after obtaining the lowpass filtered signals outputting the signals to the subtractor 750. The second microphone 730 is for collecting signals generated by the earphone loudspeaker and outputting the signals to the parameter-adjustable filter 741 and the self-adaptive parameter adjustment unit 742 in the self-adaptive filtering unit 740 when the earphone is worn. The self-adaptive parameter adjustment unit 742 is for adjusting the filtering parameters of the parameter-adjustable filter 741 according to the signals collected by the second microphone 730, the signals related to heart rate, and the preset adaptive algorithms. The parameter-adjustable filter 741 is for performing self-adaptive filtering process on the signals collected by the second microphone 730 according to filtering parameters, and outputting the first estimated signals of the signals generated by the earphone loudspeaker in the signals collected by the first microphone 720 to the subtractor 750. The subtractor 750 is for subtracting the first estimated signals outputted by the parameter-adjustable filter 741 from the signals outputted by the low pass filter, obtaining the signals related to heart rate and outputting the signals to the heart rate detection unit 760; the subtractor 750 is also for outputting the signals related to heart rate to the self-adaptive parameter adjustment unit 742. Here the self-adaptive parameter adjustment unit 742 calculates the filtering parameters of the parameter-adjustable filter 741 by using adaptive algorithms according to the inputted signals collected by the second microphone 730 and the signals related to heart rate fed back by the subtractor 750. The heart rate detection unit 760 is for detecting heart rate according to the signals related to heart rate.

In an embodiment of the invention, the heart rate detection unit 760, for detecting the cycle of the signals related to heart rate, and obtaining heart rate from the reciprocal of the detected cycle of the signals. For example, the heart rate detection unit 760 can detect the cycle of the signals related to heart rate by using existing autocorrelation method and threshold value method, etc.

Figure 8:
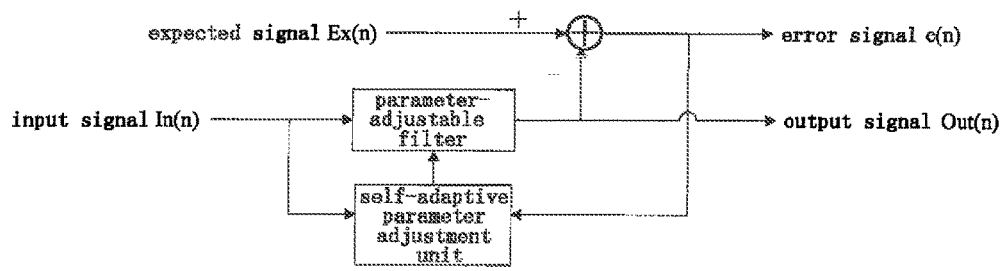
FIG. 8 is a general structural diagram of a self-adaptive filter.

FIG. 8 is a general structural diagram of a self-adaptive filter. As is shown in FIG. 8, the self-adaptive filter mainly consists of a parameter-adjustable filter and a self-adaptive parameter adjustment unit for adjusting coefficient of the filter. The self-adaptive filter does not need to know the knowledge of statistical property of the relevant signals when being designed. It can gradually "know" or estimate the required statistical property in the course of work and automatically adjust its own parameters according to this, so as to achieve the optimum filtering effect. In FIG. 8, Ex(n) is expected signal; In(n) is input signal; Out(n) is output signal; e(n) is evaluated error; and e(n)=Ex(n)−Out(n). The filtering coefficient of the self-adaptive filter is controlled by the error signal, and e(n) adjusts the self-adaptive coefficient by presetting adaptive algorithms, so that at last the mean square error of e(n) can be the smallest. Now the output signal is most approximate to the expected signal.

In the earphone shown in FIG. 7, the self-adaptive filter is adopted to perform filtering process on the signals collected by the second microphone to accurately estimate the signals generated by the earphone loudspeaker collected by the first microphone. As is shown in FIG. 7, y1(n) is the signal collected by the second microphone 730, that is the input signal in the self-adaptive filtering unit 740, and y2(n) is the output signal of the self-adaptive filtering unit 740. xL(n) represents the corresponding desired signal, and $\hat{d}(n)$ is corresponding to the error signal (mainly comprising heart rate signal). There is certain correlation between yL(n) and y1(n), thus the output signal y2(n) obtained from y1(n) via the filter can become approximate to yL(n) by designing an appropriate transfer function. For example, according to the minimum mean square error principle, when the expected value of mean square of the error signal is minimum, the output signal y2(n) can be used for estimating yL(n) effectively, and then the interference of the signals generated by the earphone loudspeaker on heart rate detection can be eliminated from the signals collected by the first microphone. The signals of the first microphone after low pass filtering subtracts the signals of the second microphone after self-adaptive filtering, obtaining the signal information $\hat{d}(n)$ related to heart rate, and on this basis heart rate can be detected. The beat of heart has certain periodicity, thus $\hat{d}(n)$ is the signal with certain periodicity. The cycle corresponding to the signal can be obtained according to autocorrelation method, and the reciprocal of the cycle is heart rate.

The specific process is as follows: suppose the signals detected by the first microphone is: x(n)=y(n)+d(n); and the signals detected by the second microphone is y1(n). Wherein y(n) represents signals generated by the earphone loudspeaker collected by the first microphone; d(n) represents the pressure change signal generated by the flow of blood; y1(n) represents signals generated by the earphone loudspeaker collected by the second microphone; and n represents sampling time point.

After low pass filtering, the signal of x(n) becomes: xL(n)=yL(n)+dL(n).

y1(n) and y(n) are both signals generated by the earphone loudspeaker. y1(n) is corresponding to the signals generated by the earphone loudspeaker collected by the second microphone, and y(n) is corresponding to the signals generated by the earphone loudspeaker collected by the first microphone. Although amplitudes of the two are different, their vibrational frequencies are the same. In order to eliminate y(n) from x(n), a self-adaptive filter (impact response is h(n)) is selected to filter y1(n), obtaining y2(n)=y1(n)*h(n), so that y2(n) can be as approximate as possible to signal yL(n) generated by the earphone loudspeaker in x(n) after low pass filtering. Thus the signals generated because of shrink of the auditory meatus can be expressed as: $\hat{d}(n)$=xL(n)−y2(n).

The self-adaptive parameter of the filter is obtained by using adaptive algorithms. There are many methods of realizing the self-adaptive algorithms. For example, the method of minimum mean square error can be adopted, that is, when the value of $E(\hat{d}^2(n))$ is minimum, obtain coefficient of the filter. After $\hat{d}(n)$ is obtained, according to the periodicity characteristic of the signal, the cycle can be detected by using autocorrelation method, threshold value method, etc, and the reciprocal of the cycle is heart rate.

Via the earphone in the embodiment shown in FIG. 5 or FIG. 7, human's heart rate can be obtained, so that the information of physical condition of human body can be obtained, or on this basis human can control their amount of exercise within an appropriate scope in accordance with specific conditions.

On the basis of aforesaid embodiment, the heart rate detection method used in an earphone of the present invention is provided. For the specific content of each step in the embodiment of the method of the invention, see the description related to the embodiment of the product of the invention.

Figure 9:
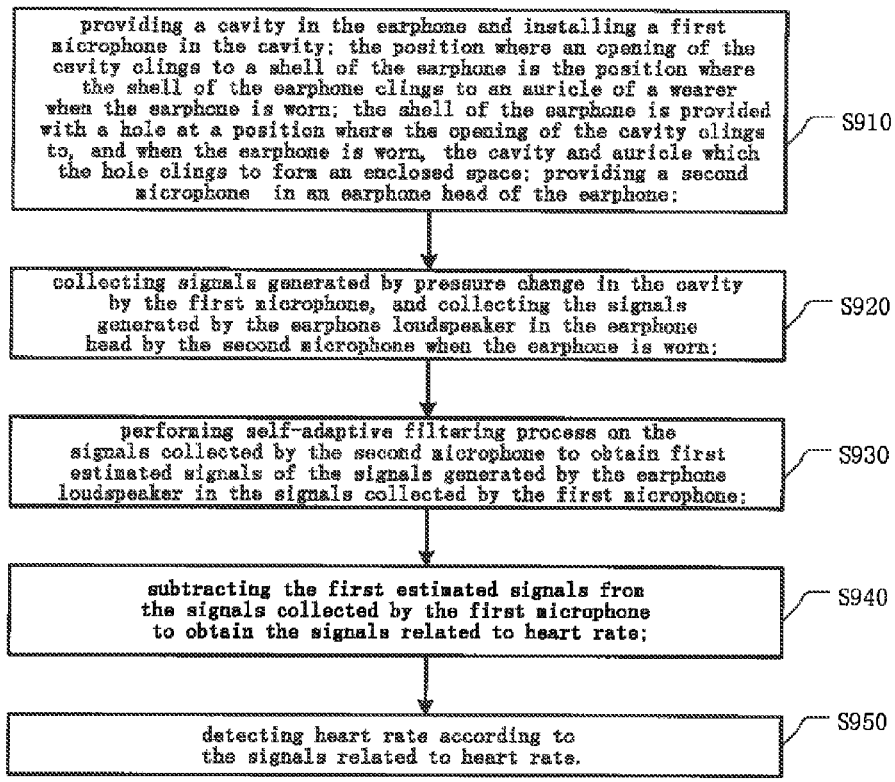
FIG. 9 is a flowchart showing a heart rate detection method used in an earphone in the embodiment of the present invention.

FIG. 9 is a flowchart showing a heart rate detection method used in an earphone in the embodiment of the present invention. As is shown in FIG. 9, the method comprises:

Step S910, providing a cavity in the earphone and installing the first microphone in the cavity; the position where an opening of the cavity clings to a shell of the earphone is the position where the shell of the earphone clings to an auricle of a wearer when the earphone is worn; the earphone shell is provided with a hole at a position where the opening of the cavity clings to, and when the earphone is worn, the cavity and the auricle which the hole clings to form an enclosed space; providing a second microphone in the earphone head of the earphone. For example, the second microphone can be provided in the earphone head at a position close to the sound production hole of the loudspeaker, see FIG. 3.

Step S920, when the earphone is worn, collecting signals generated by pressure change in the cavity by the first microphone, and collecting the signals generated by the earphone loudspeaker in the earphone head by the second microphone. Step S930, performing self-adaptive filtering process on the signals collected by the second microphone to obtain first estimated signals of the signals generated by the earphone loudspeaker in the signals collected by the first microphone. Step S940, subtracting the first estimated signals from the signals collected by the first microphone to obtain the signals related to heart rate. Step S950, detecting heart rate according to the signals related to heart rate.

In an embodiment of the invention, before subtracting the first estimated signals from the signals collected by the first microphone to obtain the signals related to heart rate, the method shown in FIG. 9 further comprises: performing low pass filtering process on the signals collected by the first microphone, obtaining low pass filtered signals. Then subtracting the first estimated signals from the signals collected by the first microphone to obtain the signals related to heart rate in Step S940 specifically comprises: subtracting the first estimated signals from the low pass filtered signals to obtain the signals related to heart rate.

In an embodiment of the invention, performing self-adaptive filtering process on the signals collected by the second microphone to obtain first estimated signals of the signals generated by the earphone loudspeaker in the signals collected by the first microphone in Step S930 comprises: calculating self-adaptive filtering parameters according to the signals collected by the second microphone, signals related to heart rate and the preset self-adaptive algorithms; performing self-adaptive filtering on the signals collected by the second microphone according to the self-adaptive filtering parameters to obtain the first estimated signals.

In an embodiment of the invention, detecting heart rate according to the signals related to heart rate in Step S950 comprises: detecting the cycle of the signals related to heart rate, and obtaining the heart rate from the reciprocal of the detected cycle of the signals.

In an embodiment of the invention, installing the second microphone in the earphone head of the earphone specifically can be: installing the second microphone in front of the vibrating diaphragm of the earphone loudspeaker and there is an interval between the second microphone and the vibrating diaphragm, so that the second microphone is situated on the transmission path of the sound wave when the earphone loudspeaker produces sound, and the second microphone and the earphone loudspeaker will not affect each other.

In summary, the beneficial effect of the technical scheme of aforesaid embodiment of the present invention comprises that: (1) The enclosed cavity of a relatively small the volume is used for placing the first microphone, which reduces interference of external noises, and reinforces signal information detected by the first microphone. (2) The second microphone is added to the earphone for collecting signals generated by the earphone loudspeaker, and the self-adaptive filter is designed to further eliminate the influence of the signals generated by the earphone loudspeaker on heart rate detection. (3) According to the feature of the frequency of pulse vibration, a low pass filter is designed to further reduce the influence of external high-frequency noise.

In addition, using earphone to detect heart rate has another critical problem, that is, it is easy to be influenced by the external interference signal, which will influence the detection of heart rate. Thus, the following solution is provided.

Figure 10:
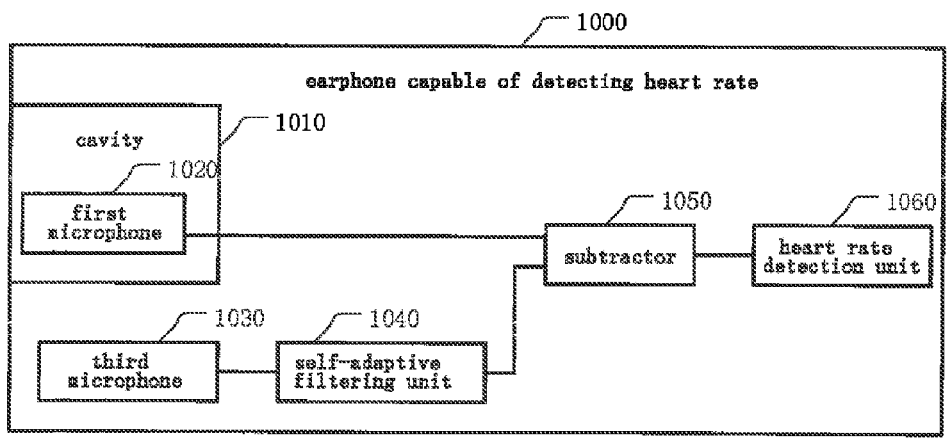
FIG. 10 is a structural diagram of an earphone capable of detecting heart rate in the embodiment of the present invention.

FIG. 10 is a structural diagram of an earphone capable of detecting heart rate in the embodiment of the present invention. As is shown in FIG. 10, the earphone 1000 capable of detecting heart rate comprises: a subtractor 1050, a heart rate detection unit 1060, a self-adaptive filtering unit 1040, a cavity 1010 provided in the earphone, a first microphone 1020 installed in the cavity 1010, and a third microphone 1030 installed in the earphone at a position where the earphone does not contact the skin of the wearer;

wherein the position wher an opening of the cavity 1010 clings to a shell of the earphone is the position where the shell of the earphone clings to an auricle of a wearer when the earphone is worn; the earphone shell is provided with a hole at a position where the opening of the cavity 1010 clings to, and when the earphone is worn, the cavity and the auricle which the hole clings to form an enclosed space.

The first microphone 1020 is for collecting signals generated by pressure change in the cavity 1010 and outputting the signals to the subtractor 1050 when the earphone 1000 is worn. The third microphone 1030 is for collecting the external interference signals and outputting the signals to the self-adaptive filtering unit 1040 when the earphone is worn. The self-adaptive filtering unit 1040 is for performing self-adaptive filtering process on the signals collected by the third microphone 1030 according to the signals related to heart rate, and after obtaining second estimated signals of the external interference signals in the signals collected by the first microphone 1020, outputting the second estimated signals to the subtractor 1050. The subtractor 1050 is for subtracting the second estimated signals outputted by the self-adaptive filtering unit 1040 from the signals collected by the microphone, obtaining the signals related to heart rate and outputting the signals to the heart rate detection unit 1060 and the self-adaptive filtering unit 1040. The heart rate detection unit 1060 is for detecting heart rate according to the signals related to heart rate.

The first microphone 1020 will collect the external interference signals while collecting signals generated by pressure change in the cavity 1010. Thus self-adaptive filtering process is performed on the signals detected by the third microphone 1030 in FIG. 10, so that the external interference signals in the signals collected by the first microphone 1020 can be accurately estimated according to the external interference signals collected by the third microphone 1030, and the purpose is to eliminate the influence of the external interference signals on the heart rate detection. The first microphone 1020 and the third microphone 1030 both will detect the external interference signals. The cycles of the two kinds of signals are the same, but amplitudes are different, thus a self-adaptive filter is needed to be used for eliminating this difference, so that the external interference signals can be eliminated from the signals collected by the first microphone 1020 to obtain effective heart rate information.

In the earphone 1000 capable of detecting heart rate shown in FIG. 10, the cavity 1010 is arranged in the earphone 1000 for placing the first microphone 1020, which reduces interference of external noises, and reinforces signal information collected by the first microphone 1020. But the external interference still exists. Thus, the earphone 1000 capable of detecting heart rate adds the third microphone 1030 to collect the external interference signals, and performs self-adaptive filtering on the signals collected by the third microphone 1030, and subtracts the third microphone signals after self-adaptive filtering from the signals collected by the first microphone 1020, and then detects heart rate. Thereby the influence of the external interference signals on the heart rate detection is further eliminated.

In an embodiment of the invention, the earphone shown in FIG. 10 further comprises a low pass filter, for performing low pass filtering process on the signals collected by the first microphone 1020, obtaining the low pass filtered signals and outputting the signals to the subtractor 1050. That is, the subtractor 1050 is for subtracting the second estimated signals outputted by the self-adaptive filtering unit 1040 from the low pass filtered signals, obtaining signals related to heart rate and outputting the signals to the heart rate detection unit 1060. This is because that the frequency of pulse vibration is relatively low (0.3 Hz-3 Hz or so) while the frequency of external noise is higher. According to this feature, the influence of external high-frequency noise can be eliminated via the low pass filter. For example, the low pass filter can be an FIR filter of which the cut-off frequency is 5 Hz. The specific structures of the cavity 1010 arranged in the earphone and the first microphone 1020 installed in the cavity 1010 are similar to the structures shown in FIG. 2A-2C, thus it will not be repeated here.

Figure 11:
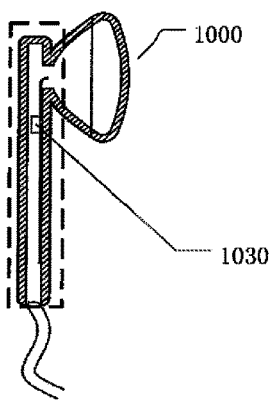
FIG. 11 is a diagram showing the installing position of a third microphone in an embodiment of the present invention.

FIG. 11 is a diagram showing the installing position of a third microphone in an embodiment of the present invention. Movement of human body will cause vibration of the skin, thus the third microphone 1030 in the embodiment is installed in the earphone 1000 at a position where the earphone does not contact the skin of the wearer, so as to avoid the influence of vibration of the skin on the signals collected by the third microphone and increase the accuracy of the signals collected by the third microphone. See FIG. 11, the third microphone 1030 can be installed in the earphone handle which connects the earphone head and the earphone wire at any position of the earphone shown by the dashed box in FIG. 11.

In practice, even if the earphone can occupy the entire auditory meatus to form a completely enclosed cavity, the influence of the external widespread infrasonic wave on heart rate detection is inevitable, because the infrasonic wave has very strong penetrating power. Thus the external interference signals will inevitably be detected by the first microphone. Then the data collected by the first microphone comprises not only the pressure change information generated by the fluctuation of pulse pressure of the vessel, but also the external interference signals. In order to eliminate the influence of the external interference signals collected by the first microphone on heart rate detection, the present invention adds a third microphone in the earphone, and the third microphone is installed in the earphone at a position where the earphone does not contact the skin of the wearer, for example, the position of the earphone shown by the dashed box in FIG. 11. The third microphone is used for collecting the external interference signals. There is a strong correlation between the external interference signals collected by the first microphone and the external interference signals collected by the third microphone, and on this basis a certain filter can be adopted to eliminate the influence of the external interference signals.

According to the foregoing analysis, if the external interference signals can be eliminated from the signals detected by the first microphone, then the signals generated by the shrink of the auditory meatus caused by flow of blood can be obtained. The signals are relevant to the frequency of heartbeat, and heart rate information can be obtained based on the signals. There is a strong correlation between the external interference signals collected by the third microphone and the external interference signals collected by the first microphone, but the two are not entirely equal. The signals cannot be directly taken out from the signals collected by the first microphone, thus the embodiment filters out the interference generated by external noises in the method of self-adaptive filtering.

In summary, in the embodiment of the invention: first, the enclosed cavity of a relatively small volume is used for placing the first microphone, which reduces interference of external noises, and reinforces signal information detected by the first microphone. Second, the third microphone is added to the earphone for collecting external interference signals, and the self-adaptive filter is designed to further eliminate the influence of the external interference signals on heart rate detection. Furthermore, according to the feature of the frequency of pulse vibration, a low pass filter is designed to further reduce the influence of external noise. It will be further described below with FIG. 12 as an example.

Figure 12:
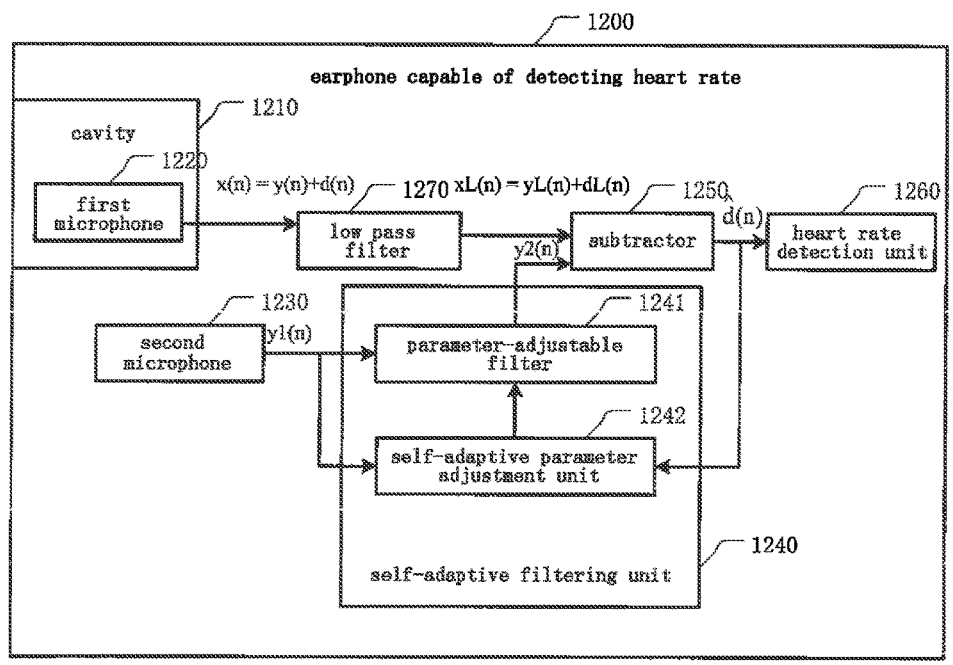
FIG. 12 is a structural diagram of an earphone capable of detecting heart rate in another embodiment of the present invention.

FIG. 12 is a structural diagram of an earphone capable of detecting heart rate in another embodiment of the present invention. As is shown in FIG. 12, the earphone 1200 capable of detecting heart rate comprises: a subtractor 1250, a heart rate detection unit 1260, a low pass filter 1270, a third microphone 1230 installed in the earphone at a position where the earphone does not contact the skin of the wearer, a self-adaptive filtering unit 1240, a cavity 1210 provided in the earphone and a first microphone 1220 installed in the cavity 1210. Wherein the self-adaptive filtering unit 1240 comprises: a parameter-adjustable filter 1241 and a self-adaptive parameter adjustment unit 1242.

Wherein the position where an opening of the cavity 1210 clings to a shell of the earphone is the position where the shell of the earphone clings to an auricle of a wearer when the earphone is worn; the shell of the earphone is provided with a hole at a position where the opening of the cavity 1210 clings to, and when the earphone is worn, the cavity and the auricle which the hole clings to form an enclosed space.

The first microphone 1220 is used for collecting signals generated by pressure change in the cavity 1210 and outputting the signals to the low pass filter 1270 when the earphone 1200 is worn. The first microphone 1220 will collect the external interference signals while collecting signals generated by pressure change in the cavity 1210. The low pass filter 1270 is for performing low pass filtering process on signals collected by the first microphone 1220 and after obtaining the lowpass filtered signals outputting the signals to the subtractor 1250. The third microphone 1230 is for collecting external interference signals and outputting the signals to the parameter-adjustable filter 1241 and the self-adaptive parameter adjustment unit 1242 in the self-adaptive filtering unit 1240 when the earphone is worn. The self-adaptive parameter adjustment unit 1242 is for adjusting the filtering parameters of the parameter-adjustable filter 1241 according to the signals collected by the third microphone 1230, the signals related to heart rate, and the preset adaptive algorithms. The parameter-adjustable filter 1241 is for performing self-adaptive filtering process on the signals collected by the third microphone 1230 according to filtering parameters, and outputting the second estimated signals of the external interference signals in the signals collected by the first microphone 1220 to the subtractor 1250. The subtractor 1250 is for subtracting the second estimated signals outputted by the parameter-adjustable filter 1241 from the signals outputted by the low pass filter, obtaining the signals related to heart rate and outputting the signals to the heart rate detection unit 1260; the subtractor 1250 is also for outputting the signals related to heart rate to the self-adaptive parameter adjustment unit 1242. Here the self-adaptive parameter adjustment unit 1242 calculates the filtering parameters of the parameter-adjustable filter 741 by using self-adaptive algorithms according to the inputted signals collected by the third microphone 1230 and the signals related to heart rate fed back by the subtractor 1250. The heart rate detection unit 1260 is for detecting heart rate according to the signals related to heart rate.

In an embodiment of the invention, the heart rate detection unit 1260 is for detecting the cycle of the signals related to heart rate, and obtaining heart rate from the reciprocal of the detected cycle of the signals. For example, the heart rate detection unit 1260 can detect the cycle of the signals related to heart rate by using existing autocorrelation method and threshold value method, etc. The general structure of self-adaptive filter is shown in FIG. 8.

In the earphone shown in FIG. 12, the self-adaptive filter is adopted to perform filtering process on the signals collected by the third microphone to accurately estimate the external interference signals collected by the first microphone. As is shown in FIG. 12, y1(n) is the signals collected by the third microphone 1230, that is, the input signal in the self-adaptive filtering unit 1240, and y2(n) is the output signal of the self-adaptive filtering unit 1240. xL(n) represents the corresponding desired signal, and $\hat{d}(n)$ is corresponding to the error signal (mainly comprising heart rate signal). There is certain correlation between yL(n) and y1(n), thus the output signal y2(n) obtained from y1(n) via the filter can become approximate to yL(n) by designing an appropriate transfer function. For example, according to the minimum mean square error principle, when the expected value of mean square of the error signal is minimum, the output signal y2(n) can effectively estimate yL(n), and then the interference of the external interference signals on heart rate detection can be eliminated from the signals collected by the first microphone, so the influence of the external interference signals is eliminated once more. The signals of the first microphone after low pass filtering subtracts the signals of the third microphone after self-adaptive filtering, obtaining the signal information $\hat{d}(n)$ related to heart rate, and on this basis heart rate can be detected. The beat of heart has certain periodicity, thus $\hat{d}(n)$ is the signal with certain periodicity. The cycle corresponding to the signal can be obtained according to autocorrelation method, and the reciprocal of the cycle is heart rate.

The specific process is as follows: suppose the signals detected by the first microphone is: x(n)=y(n)+d(n); and the signals detected by the third microphone is y1(n). Wherein y(n) represents the external interference signals collected by the first microphone; d(n) represents the pressure change signal generated by the flow of blood; y1(n) represents the external interference signals collected by the third microphone; and n represents sampling time point.

After low pass filtering, the signal of x(n) becomes: xL(n)=yL(n)+dL(n).

y1(n) and y(n) are both external interference signals. y1(n) is corresponding to the external interference signals collected by the third microphone, and y(n) is corresponding to the external interference signals collected by the first microphone. Although amplitudes of the two are different, their vibrational frequencies are the same. In order to eliminate y(n) from x(n), a self-adaptive filter (impact response is h(n)) is selected to filter y1(n), obtaining y2(n)=y1(n)*h(n), so that y2(n) can be as approximate as possible to the external interference signals yL(n) in x(n) after low pass filtering.

Thus the signals generated because of shrink of the auditory meatus can be expressed as: $\hat{d}(n)$=xL(n)−y2(n). The self-adaptive parameter of the filter is obtained by using self-adaptive algorithms. There are many methods of realizing the self-adaptive algorithms. For example, the method of minimum mean square error can be adopted, that is, when the value of $E(\hat{d}^2(n))$ is minimum, obtain the coefficient of the filter. After $\hat{d}(n)$ is obtained, according to the periodicity characteristic of the signal, the cycle can be detected by using autocorrelation method, threshold value method, etc, and the reciprocal of the cycle is heart rate.

Via the earphone in the embodiment shown in FIG. 10 or FIG. 12, human's heart rate can be obtained, so that the information of physical condition of human body can be obtained, or on this basis human can control their amount of exercise within an appropriate scope in accordance with specific conditions.

On the basis of aforesaid embodiment, the heart rate detection method used in an earphone of the present invention is provided. For the specific content of each step in the embodiment of the method of the invention, see the description related to the embodiment of the product of the invention.

Figure 13:
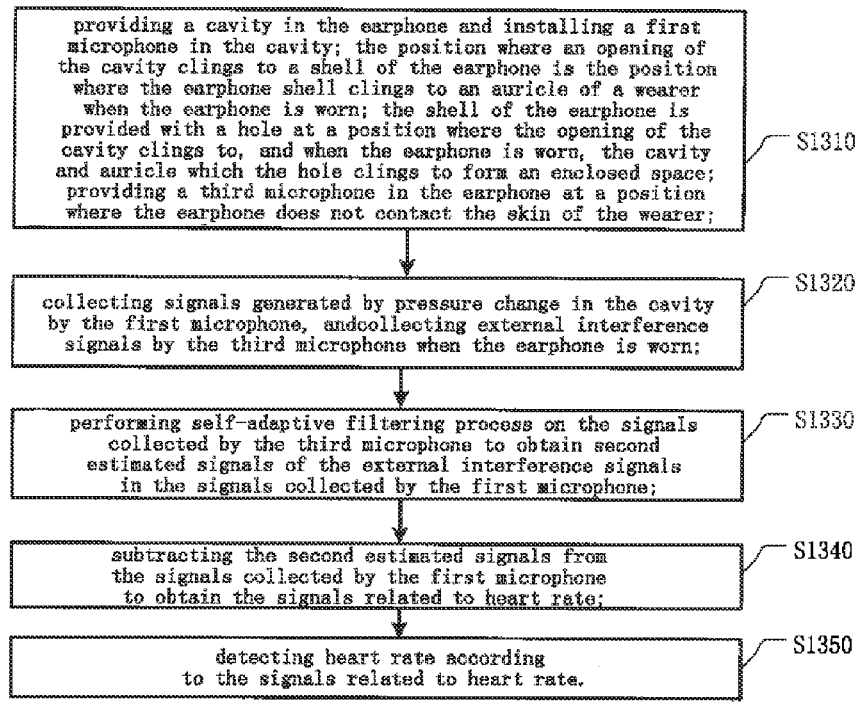
FIG. 13 is a flowchart showing a heart rate detection method used in an earphone in the embodiment of the present invention.

FIG. 13 is a flowchart showing a heart rate detection method used in an earphone in the embodiment of the present invention. As is shown in FIG. 13, the method comprises:

Step S1310, providing a cavity in the earphone and installing a first microphone in the cavity; the position where an opening of the cavity clings to a shell of the earphone is the position where the shell of the earphone clings to an auricle of a wearer when the earphone is worn; the shell of the earphone is provided with a hole at a position where the opening of the cavity clings to, and when the earphone is worn, the cavity and the auricle which the hole clings to form an enclosed space; and providing a third microphone in the earphone at a position where the earphone does not contact the skin of the wearer. For example, the third microphone can be installed in the earphone handle which connects the earphone head and the earphone wire, see FIG. 3.

Step S1320, when the earphone is worn, collecting signals generated by pressure change in the cavity by the first microphone, and collecting the external interference signals by the third microphone. Step S1330, performing self-adaptive filtering process on the signals collected by the third microphone to obtain second estimated signals of the external interference signals in the signals collected by the first microphone. Step S1340, subtracting the second estimated signals from the signals collected by the first microphone to obtain the signals related to heart rate. Step S1350, detecting heart rate according to the signals related to heart rate.

In an embodiment of the invention, before subtracting the second estimated signals from the signals collected by the first microphone to obtain the signals related to heart rate, the method shown in FIG. 13 further comprises: performing low pass filtering process on the signals collected by the first microphone, obtaining low pass filtered signals. Then subtracting the second estimated signals from the signals collected by the first microphone to obtain the signals related to heart rate in Step S1340 specifically comprises: subtracting the second estimated signals from the low pass filtered signals to obtain the signals related to heart rate.

In an embodiment of the invention, performing self-adaptive filtering process on the signals collected by the third microphone to obtain second estimated signals of the external interference signals in the signals collected by the first microphone in Step S1330 comprises: calculating self-adaptive filtering parameters according to the signals collected by the third microphone, signals related to heart rate and the preset self-adaptive algorithms; performing self-adaptive filtering on the signals collected by the third microphone according to the self-adaptive filtering parameters to obtain the second estimated signals.

In an embodiment of the invention, detecting heart rate according to the signals related to heart rate in Step S1350 comprises: detecting the cycle of the signals related to heart rate, and obtaining the heart rate from the reciprocal of the detected cycle of the signals.

In summary, the beneficial effect of the technical scheme of the present invention comprises that: (1) the enclosed cavity of a relatively small volume is used for placing the first microphone, which reduces interference of external noises, and reinforces signal information detected by the first microphone. (2) The third microphone is added to the earphone for collecting external interference signals, and the self-adaptive filter is designed to further eliminate the influence of the external interference signals on heart rate detection. (3) According to the feature of the frequency of pulse vibration, a low pass filter is designed to further reduce the influence of external high-frequency noise.

In an embodiment of the invention, the earphone can be equipped with the first microphone, the second microphone and the third microphone simultaneously, in order to eliminate the influence of the signals generated by the earphone loudspeaker on heart rate detection and the influence of the external interference signals on heart rate detection, wherein for the specific way of installing the three microphones, see relevant content of aforesaid embodiments.

Figure 14:
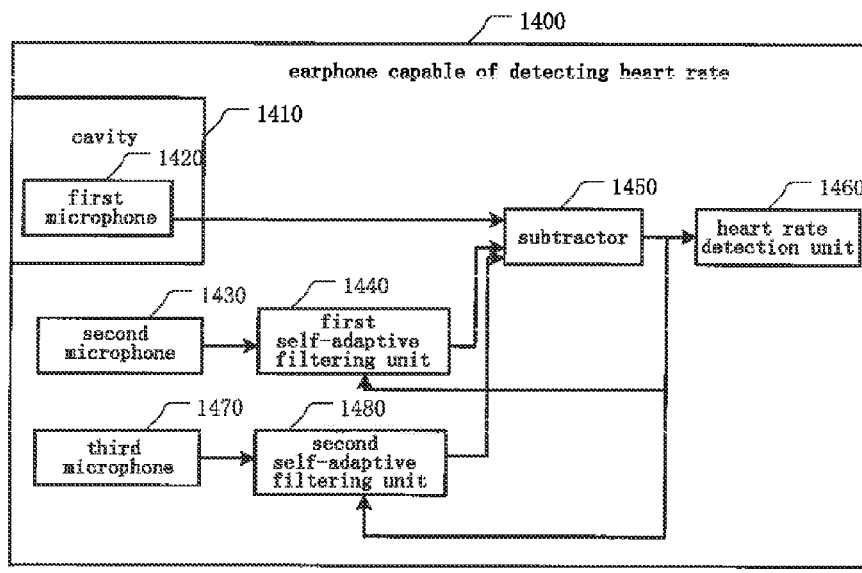
FIG. 14 is a structural diagram of an earphone capable of detecting heart rate in another embodiment of the present invention.

FIG. 14 is a structural diagram of an earphone capable of detecting heart rate in another embodiment of the present invention. As is shown in FIG. 14, the earphone 1400 capable of detecting heart rate comprises: a cavity 1410 provided in the earphone, a first microphone 1420 installed in the cavity 1410, a second microphone 1430, a first self-adaptive filtering unit 1440, a subtractor 1450, a heart rate detection unit 1460, a third microphone 1470 and a second self-adaptive filtering unit 1480.

As can be seen, the embodiment shown in FIG. 14 combines the schemes shown in FIG. 5 and FIG. 10, and the realizing function of each functional unit is correspondently the same. The subtractor needs to be described here. The subtractor 1450 is for subtracting the first estimated signals (obtained by performing self-adaptive filtering on the signals collected by the second microphone) and the second estimated signals (obtained by performing self-adaptive filtering on the signals collected by the third microphone) from the signals collected by the first microphone. The subtractor 1450 can be understood as being equivalent to a cascade of the subtractor 550 and the subtracor 1050. In FIG. 14, the subtractor 1450 can be replaced with cascaded first subtractor and second subtractor. By now: the output of the first microphone 1420 and output of the first self-adaptive filtering unit 1440 are connected with the input of the first subtractor; the output of the second self-adaptive filtering unit 1480 and output of the first subtractor are connected with the input of the second subtractor; the second subtractor is for subtracting the output signal of the second self-adaptive filtering unit 1480 (i.e. the second estimated signals) from the output signal of the first subtractor (i.e. the signal obtained after the signals collected by the first microphone subtract the first estimated signals), obtaining the signals related to heart rate and outputting the signals to the heart rate detection unit, and feeding back to the second self-adaptive filtering unit 1480 and the first self-adaptive filtering unit 1440.

The earphone illustrated in FIG. 14 can eliminate the influence of signals produced by the earphone loudspeaker on heart rate detection and the influence of external interference signal on heart rate detection.

The foregoing descriptions merely show preferred embodiments of the present invention, and are not intended to limit the protection scope of the present invention. Any modification, equivalent replacement and improvement made within the spirit and principle of the present invention shall fall into the protection scope of the present invention.

The invention claimed is:

1. A heart rate detection method used in an earphone, said heart rate detection method comprises:

providing a cavity inside the earphone, and installing a first microphone in said cavity; a position where an opening of said cavity clings to a shell of the earphone is a position where the shell of the earphone clings to an auricle of an ear of a wearer when the earphone is worn; the shell of the earphone is provided with a hole at the position where the opening of said cavity clings to, and when the earphone is worn on the ear of the wearer, said cavity and the auricle which said hole clings to form an enclosed space;

collecting signals generated by pressure change in said cavity by the first microphone when the earphone is worn;

taking the signals collected by the first microphone as signals related to heart rate; and detecting heart rate according to the signals related to heart rate.

2. The heart rate detection method according to claim 1, wherein the method further comprises:

performing low pass filtering process on the signals collected by the first microphone to filter out high-frequency interference signals;

taking the low pass filtered signals as said signals related to heart rate;

said detecting heart rate according to the signals related to heart rate comprising: detecting the cycle of said signals related to heart rate, and obtaining, the heart rate from the reciprocal of the detected cycle of the signals.

3. The heart rate detection method according to claim 1, wherein the method further comprises:

installing a second microphone in an earphone head of the earphone;

collecting signals generated by an earphone loudspeaker in the earphone head by said second microphone when the earphone is worn;

performing self-adaptive filtering process on the signals collected by said second microphone to obtain first estimated signals of the signals generated by the earphone loudspeaker in the signals collected by the first microphone; and subtracting said first estimated signals from the signals collected by the first microphone to obtain the signals related to heart rate.

4. The heart rate detection method according to claim 3, wherein said performing self-adaptive filtering process on the signals collected by said second microphone to obtain first estimated signals of the signals generated by the earphone loudspeaker in the signals collected by the first microphone comprises:

calculating self-adaptive filtering parameters according to the signals collected by the second microphone, signals related to heart rate and preset self-adaptive algorithms; and performing self-adaptive filtering on the signals collected by the second microphone according to said self-adaptive filtering parameters to obtain said first estimated signals.

5. The heart rate detection method according to claim 3, wherein the method further comprises:

installing a third microphone in the earphone at a position where the earphone does not contact the skin of the wearer;

collecting external interference signals by said third microphone when the earphone is worn;

performing self-adaptive filtering process on the signals collected by said third microphone to obtain second estimated signals of the external interference signals in the signals collected by the first microphone;

said taking the signals collected by the first microphone as signals related to heart rate comprising: subtracting the second estimated signals from the signals collected by the first microphone to obtain the signals related to heart rate;

said subtracting the first estimated signals from the signals collected by the first microphone to obtain the signals related to heart rate comprising: subtracting said first estimated signals and said second estimated signals from the signals collected by the first microphone to obtain the signals related to heart rate.

6. The heart rate detection method according to claim 5, wherein said performing self-adaptive filtering process on the signals collected by said third microphone to obtain second estimated signals of external interference signals in the signals collected by the first microphone comprises:

calculating self-adaptive filtering parameters according to the signals collected by the third microphone, signals related to heart rate and preset self-adaptive algorithms; and performing self-adaptive filtering on the signals collected by the third microphone according to said self-adaptive filtering parameters to obtain said second estimated signals.

7. An earphone capable of detecting heart rate, wherein the earphone comprises: a signal processor, a cavity provided in the earphone, and a first microphone installed in said cavity;

wherein a position where an opening of said cavity clings to a shell of the earphone is a position where the shell of the earphone clings to an auricle of an ear of a wearer when the earphone is worn; the earphone shell is provided with a hole at the position where the opening of said cavity clings to, and when the earphone is worn on the ear of the wearer, said cavity and the auricle which said hole clings to form an enclosed space;

said first microphone is configured to collect signals generated by pressure change in said cavity when the earphone is worn; the signals collected by the first microphone are taken as signals related to heart rate; and said signal processor is configured to detect heart rate according to the signals related to heart rate.

8. The earphone according to claim 7, wherein the earphone further comprises:

a low pass filter configured to perform low pass filtering process on the signals collected by said first microphone to filter out high-frequency interference signals; and correspondingly, taking the low pass filtered signals as said signals related to heart rate.

9. The earphone according to claim 7, wherein
the signal processor is configured to detect the cycle of said signals related to heart rate, and obtaining heart rate from the reciprocal of the detected cycle of the signals.

10. The earphone according to claim 7, wherein the earphone further comprises: a first subtractor, and a second microphone installed in the earphone head of the earphone;

said second microphone is configured to collect signals generated by an earphone loudspeaker and output the signals to said signal processor;

said signal processor is configured to perform self-adaptive filtering process on the signals collected by said second microphone according to the signals related to heart rate to obtain first estimated signals of the signals generated by the earphone loudspeaker in the signals collected, by the first microphone, and output the first estimated signals to said first subtractor; and said first subtractor is configured to subtract said first estimated signals from the signals collected by the first microphone to obtain the signals related to heart rate, and output the signals related to heart rate to said signal processor.

11. The earphone according to claim 10, wherein
said second microphone is arranged in front of a vibrating diaphragm of the earphone loudspeaker and there is an interval between the second microphone and the vibrating diaphragm, so that the second microphone is situated on the transmission path of a sound wave when the earphone loudspeaker produces sound, and the second microphone and the earphone loudspeaker do not affect each other.

12. The earphone according to claim 10, wherein said signal processor comprises: a first parameter-adjustable filter;

said second microphone is configured to output the collected signals to said signal processor;

said first subtractor is configured to output said signals related to heart rate to said signal processor;

said signal processor is configured to adjust filtering parameters of said first parameter-adjustable filter according to the signals collected by the second microphone, the signals related to heart rate, and preset self-adaptive algorithms; and said first parameter-adjustable filter is configured to perform self-adaptive filtering on the signals collected by the second microphone according to the filtering parameters, and output the first estimated signals of the signals generated by the earphone loudspeaker in the signals collected by the first microphone to said first subtractor.

13. The earphone according to claim 10, wherein the earphone further comprises: a second subtractor, and a third microphone installed in the earphone at a position where the earphone does not contact the skin of the wearer;

said third microphone is configured to collect external interference signals and output the external interference signals to said signal processor when the earphone is worn;

said signal processor is configured to perform self-adaptive filtering process on the signals collected by said third microphone according to the signals related to heart rate to obtain second estimated signals of the external interference signals in the signals collected by the first microphone, and output the second estimated signals to said second subtractor; and said second subtractor is configured to subtract said second estimated signals from the signals collected by the first microphone obtain the signals related to heart rate, and output the signals related to heart rate to said signal processor; or configured to subtract said second estimated signal from the signals collected by the first microphone that have subtracted said first estimated signals to obtain the signals related to heart rate, and output the signals related to heart rate to said signal processor.

14. The earphone according to claim 13 wherein said third microphone is provided in the earphone handle which connects the earphone head and an earphone wire.

15. The earphone according to claim 13, wherein said signal processor comprises: a second parameter-adjustable filter;
- said third microphone is configured to output the collected signals to said signal processor;
- said second subtractor is configured to output said signals related to heart rate to said signal processor;
- said signal processor is configured to adjust filtering parameters of said second parameter-adjustable filter according to the signals collected by the third microphone, the signals related to heart rate, and preset self-adaptive algorithms; and
- said second parameter-adjustable filter is configured to perform self-adaptive filtering on the signals collected by the third microphone according to the filtering parameters, and output the second estimated signals of the external interference signals in the signals collected by theist microphone to said second subtractor.

* * * * *